United States Patent
Bercot et al.

(10) Patent No.: US 9,296,735 B2
(45) Date of Patent: Mar. 29, 2016

(54) METHOD FOR THE PREPARATION OF THIADIAZOLES

(71) Applicant: AMGEN INC., Thousand Oaks, CA (US)

(72) Inventors: Eric A. Bercot, Bend, OR (US); Matthew Bio, Santa Barbara, CA (US); Johann Chan, Westlake Village, CA (US); John Colyer, Newbury Park, CA (US); Yuanqing Fang, Belmont, MA (US); Steven Mennen, Boston, MA (US); Robert R. Milburn, Thousand Oaks, CA (US); Jason Tedrow, Santa Monica, CA (US); Babak Riahi, Woodland Hills, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 14/402,069

(22) PCT Filed: May 17, 2013

(86) PCT No.: PCT/US2013/041504
§ 371 (c)(1),
(2) Date: Nov. 18, 2014

(87) PCT Pub. No.: WO2013/173672
PCT Pub. Date: Nov. 21, 2013

(65) Prior Publication Data
US 2015/0141655 A1    May 21, 2015

Related U.S. Application Data

(60) Provisional application No. 61/648,928, filed on May 18, 2012.

(51) Int. Cl.
C07D 285/08 (2006.01)
C07D 417/04 (2006.01)
C07D 317/26 (2006.01)

(52) U.S. Cl.
CPC ............ *C07D 417/04* (2013.01); *C07D 317/26* (2013.01)

(58) Field of Classification Search
CPC ..... C07D 285/08; C07D 271/07; A01N 43/82; A61K 31/045; A61K 31/075
USPC .......................................... 548/129; 549/453
See application file for complete search history.

(56) References Cited

U.S. PATENT DOCUMENTS

2010/0204240 A1* 8/2010 Aicher ................. C07D 417/14
  514/252.03

FOREIGN PATENT DOCUMENTS

| EP | 0120289 A2 | 10/1984 |
| JP | 4144978 B2 | 9/2008 |
| WO | 2007053345 A1 | 5/2007 |
| WO | 2007089512 A1 | 8/2007 |
| WO | 2007117381 A1 | 10/2007 |
| WO | 2008091770 A1 | 7/2008 |
| WO | 2008118718 A1 | 10/2008 |
| WO | 2009042435 A1 | 4/2009 |

OTHER PUBLICATIONS

Althoff, W., et al., Arch. Pharm. (Weinheim) 314, 518-524 (1981) with English Abstract.
Castro, A., et al., Bioorganic & Medicinal Chemistry 14 (2006) 1644-1652.
De Alvarenga, E.S., et al., J. Chil. Chem. Soc., 51, No. 3 (2006) 986-988.
March, J., Advanced Organic Chemistry, Reactions, Mechanisms, and Structure, Third Edition, John Wiley & Sons, 1985, pp. 359-360, 795-796, and 854-855.
Schmid, C.R., et al., J. Org. Chem., 1991, 56, 4056-4058.
BASF Technical Leaflet, Apr. 1999, Sodium Metabisulfite Grades, 8 pages.
International Search Report and Written Opinion corresponding to related PCT Application No. PCT/US13/41504 mailed Oct. 31, 2013; 15 pages.

\* cited by examiner

*Primary Examiner* — Alicia L Otton
*Assistant Examiner* — Sagar Patel
(74) *Attorney, Agent, or Firm* — Sarah S. Mastous; Viksnins Harris & Padys PLLP

(57) ABSTRACT

The present invention relates to processes for preparing protected glyceraldehydes, such as (hydroxy)methanesulfonates. In addition, the invention relates to thiadiazoles, particularly 3-diooxolanyl-thiadiazoles.

5 Claims, No Drawings

METHOD FOR THE PREPARATION OF THIADIAZOLES

RELATED APPLICATIONS

This application is a 371 filing of PCT Application No. PCT/US2013/041504, filed May 17, 2013, which claims priority to U.S. Provisional Application No. 61/648,928 filed May 18, 2012, each of which is incorporated herein by reference in its entirety.

FIELD OF THE INVENTION

The present invention relates to processes for preparing protected glyceraldehydes, such as (hydroxy)methanesulfonates. In addition, the invention relates to processes for preparing thiadiazoles, particularly arylthio-substituted thiadiazoles.

BACKGROUND OF THE INVENTION

Hydroxy-containing compounds are useful as medicines. However, their reactivity can cause difficulties in their synthesis. Thiadiazoles are also useful in medicinal chemistry. Because of the complex mechanism involved, there exists high variability in the preferred conditions for alternative synthesis of thiadiazoles. Protected glyceraldehydes are valuable chiral starting materials. However they are plagued by their instability.

PCT publications WO09/042435 and WO07/117381 describe an in situ process of preparing substituted thiadiazoles from activated thiocyanates. Amino-substituted thiadiazoles prepared from the acyl thioisocyanates is described in JP4144978.

Althoff et al. [Archiv. der Pharmazie 314, 1981, p 518-524] describe the preparation of related bisulfite adducts from the corresponding cyano dioxolanes. Schmid, C. R. et al [J. Org. Chem, 1991, 56, 4056-4058] describe the preparation of (4R)-2,2-dimethyl-1,3-dioxolane-4-carbaldehyde.

There is an ongoing need for more facile and higher yielding processes for preparing such protected glyceraldehydes and thiadiazoles.

DESCRIPTION OF THE INVENTION

The present invention is generally directed to glyceraldehyde bisulfite adducts and processes for preparing them.

The present invention is directed to formation of substituted sulfide-thiadiazoles and thiadiazole sulfones.

Another embodiment of the invention is directed to formation of 5-substituted thio-thiadiazoles from the corresponding oximes.

It is believed the chemical formulas and names used herein correctly and accurately reflect the underlying chemical compounds. However, the nature and value of the present invention does not depend upon the theoretical correctness of these formulas, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer.

The following definitions are provided for the full understanding of terms and abbreviations used in this specification.

The abbreviations in the specification correspond to units of measure, techniques, properties, or compounds as follows:

Anh. Anhydrous
$CH_2Cl_2$ DCM dichloromethane, methylene chloride
DIPEA di-isopropylethylamine
DMAC N,N-dimethylacetamide
DMF dimethylformamide
EtOAc ethyl acetate
EtOH ethanol
h hour(s)
HCl hydrochloric acid
$H_2O$ water
$H_2O_2$ hydrogen peroxide
$HSO_3^-$ bisulfate
IPA isopropyl alcohol
IPAC isopropyl acetate
Kg kilogram
$K_2S_2O_5$ potassium metabisulfite
$K_2CO_3$ potassium carbonate
L liter
LJR Liter jacketed reactor
MeTHF 2-methyl tetrahydrofuran
M molar
mCPBA metachloroperbenzoic acid
MeCN acetonitrile
MeOH methanol
$MgSO_4$ magnesium sulfate
Min minutes
mL milliliter(s)
mM millimolar
mmole millimole(s)
MMPP Magnesium monoperoxyphthalate hexahydrate
$MoO_2Cl_2$ Molybdenum dichloride dioxide
$MoO_2(acac)_2$ Molybdenyl(VI) acetylacetonate
MsCl mesyl chloride, methylsulfonyl chloride
MTBE methyl tertbutyl ether
$N_2$ nitrogen
NCS N-chlorosuccinimide
NMO N-Methylmorpholine-N-oxide
$NH_2OH$ hydroxylamine
$NH_2OH$ HCl hydroxylamine hydrochloride
$(NH_4)_6Mo_7O_{24}$ ammonium molybdate
$(NH_4)_6Mo_7O_{24}$—$(H_2O)_4$ ammonium molybdenate tetrahydrate
NaSCN sodium thiocyanate
$NaHCO_3$ sodium bicarbonate
$Na_2CO_3$ sodium carbonate
$NaIO_4$ sodium iodate
$NaHSO_3$ sodium bisulfite
NaOAc sodium acetate
$Na_2SO_3$ sodium sulfite
$Na_2S_2O_5$ sodium metabisulfite
$NaWO_4$ sodium tungstate
$Pb(OAc)_4$ Lead tetraacetate
RT room temperature
Sat. saturated
TBHP tert-Butyl hydroperoxide
THF tetrahydrofuran
TPAP tetrapropylammonium perruthenate
UHP urea-$H_2O_2$
μL microliter(s)

GENERAL PROCEDURE

Scheme A

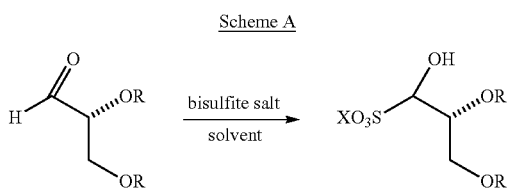

The present invention, as shown in Scheme A, involves formation of protected alcohols via treatment of corresponding aldehydes with a salt of $SO_3^{-2}$, such as $Na_2S_2O_5$, $NaHSO_3$, $Na_2SO_3$, or $K_2S_2O_3$, where X is a cation, where R is aryl, alkyl or the two R groups together form cycloalkyl or spirocycloalkyl. An organic solvent, preferably one that is miscible in water is used. Examples of such solvents include alcohols, such as EtOH, MeOH, IPA and propyl alcohol; ethers, such as THF, DMF, ethylene glycol, and the like.

Scheme B

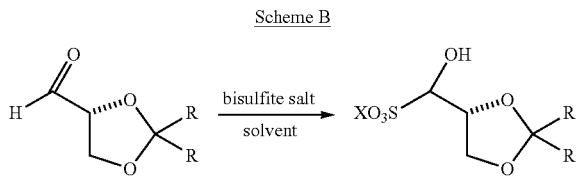

The present invention, as shown in Scheme B, involves formation of protected glyceraldehydes via treatment of corresponding aldehydes with a salt of $SO_3^{-2}$, such as $Na_2S_2O_5$, $NaHSO_3$, $Na_2SO_3$, or $K_2S_2O_5$, where X is a cation, and R is aryl, alkyl or the two R groups together form cycloalkyl. A solvent mixture comprising a water miscible organic solvent, and water can be used. Examples of such solvents include alcohols, such as EtOH, MeOH, IPA and propyl alcohol; ethers, such as THF, ethylene glycol, and the like.

The present invention involves treatment of protected glyceraldehydes with a salt of bisulfite where R is alkyl or together form cycloalkyl. The present invention involves protected glyceraldehydes where R is $C_{1-6}$ alkyl or together forms $C_{3-6}$ cycloalkyl. The present invention involves protected glyceraldehydes where both R groups are the same.

In some embodiments, the present invention is directed to processes for preparing bisulfite adducts of glyceraldehydes, comprising the steps of: treating an aldehyde with $Na_2S_2O_5$ in a solvent mixture such as EtOH and water.

Scheme C

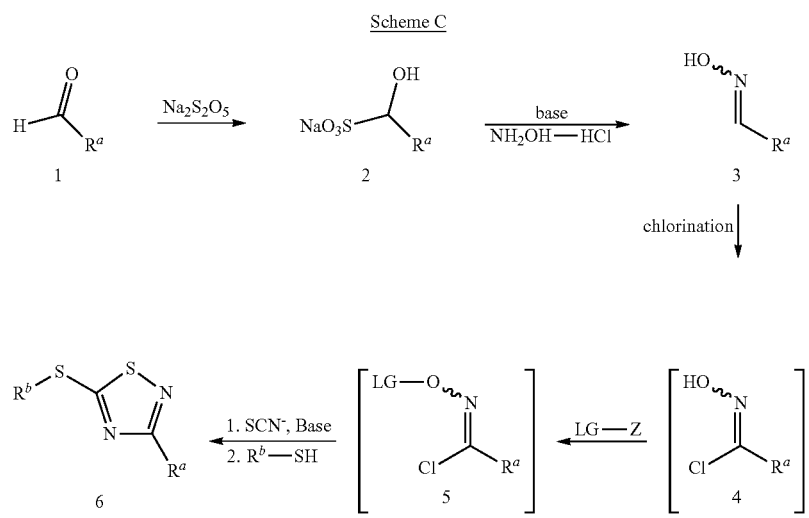

The present invention, as shown in Scheme C, involves formation of the thiadiazole sulfides 6, where $R^b$ is aryl, alkyl, arylalkyl, or 5-6 membered heterocyclyl and $R^a$ is aryl, alkyl, arylalkyl, or 5-6 membered heterocyclyl. In another embodiment of the invention, $R^a$ is $C_{6-10}$ membered aryl, $C_{1-6}$ alkyl, $C_{6-10}$ aryl-$C_{1-3}$ alkyl, 5-6 membered heteroaryl or 5-6 membered saturated heterocyclyl. In another embodiment of the invention, $R^a$ is a 5-6 membered oxygen containing saturated heterocyclyl. In another embodiment of the invention, $R^a$ is a protected diol. In another embodiment of the invention, $R^b$ is $C_{6-10}$ membered aryl, $C_{1-6}$ alkyl, $C_{6-10}$ aryl-$C_{1-3}$ alkyl, 5-6 membered heteroaryl or 5-6 membered saturated or partially saturated heterocyclyl. In another embodiment of the invention, the aryl, alkyl, arylalkyl, or 5-6 membered heterocyclyl substitutents are optionally substituted with one or more substituents selected from lower alkyl, halo, haloalkyl, and the like.

Treatment of an aldehyde 1 with a salt of $SO_3^{-2}$, such as $Na_2S_2O_5$, $NaHSO_3$, or $Na_2SO_3$, at a temperature above RT, preferably at above 35° C., more preferably at a temperature of about 50° C., provides a diastereomeric mixture of the bisulfite adduct 2. Embodiments of the process include treatment with $Na_2S_2O_5$ in an amount of about 0.5-2 equivalents per mole of the aldehyde employed. The invention also relates to the use of about 0.5 equivalents of $Na_2S_2O_5$.

Treatment of the bisulfite adduct 2 in an organic solvent, such as MeTHF, with an aqueous solution of $NH_2OH$—HCl and a base, such as $K_2CO_3$ or $Na_2CO_3$, gives the oxime 3. To the anh. oxime 3 in a solvent such as a mixture of DMAC/MeTHF, is added a catalytic amount of HCl in a solvent such as dioxane followed by halogenation, such as with Cl₂ or NCS, gives the corresponding chloro-oxime 4 intermediate. The chloro-oxime 4 is provided with a leaving group, such as with treatment with MsCl [LG is Ms] in the presence of base, such as DIPEA, to give the chloro-compound 5, at a temperature below RT, preferably at a temperature of about 0° C. Alternatively, LG is tosyl or an acetate. Reaction of chloro-compound 5 with SCN⁻, in a solvent such as MeTHF, at a temperature of about RT, and in the presence of organic base, such as pyridine, gives the acyl thioisocyanate intermediate. Treatment of the acyl thioisocyanate with a substituted thiol, such as toluene sulfide, in the presence of 1-2 equivalents of organic base, such as pyridine, in a non-polar solvent such as MeTHF, at a temperature below RT, preferably at about 0° C., gives 1,2,4-thiadiazole 6.

The invention also relates to a process in an atmosphere where minimal oxygen is present, such as in a N₂ environment.

The present invention also relates to a process where the bisulfite adduct 2 is isolated prior to the cyclization step. Alternatively, the bisulfite adduct 2 is not isolated prior to formation of the thiadiazole.

Embodiments of the process include reaction in a non-aqueous solvent environment. Such solvents include MeTHF, MTBE, IPAC, heptane, hexane, toluene, benzene, xylenes, IPA, dioxane, CH₂Cl₂, EtOH, MeCN and THF. The present invention also relates to a process where a mixture of solvents is utilized. In certain embodiments of the invention, MeTHF is used as the solvent. Where the term "non-aqueous" is used, it is not to intend that water is not generated by a reaction step.

Scheme D

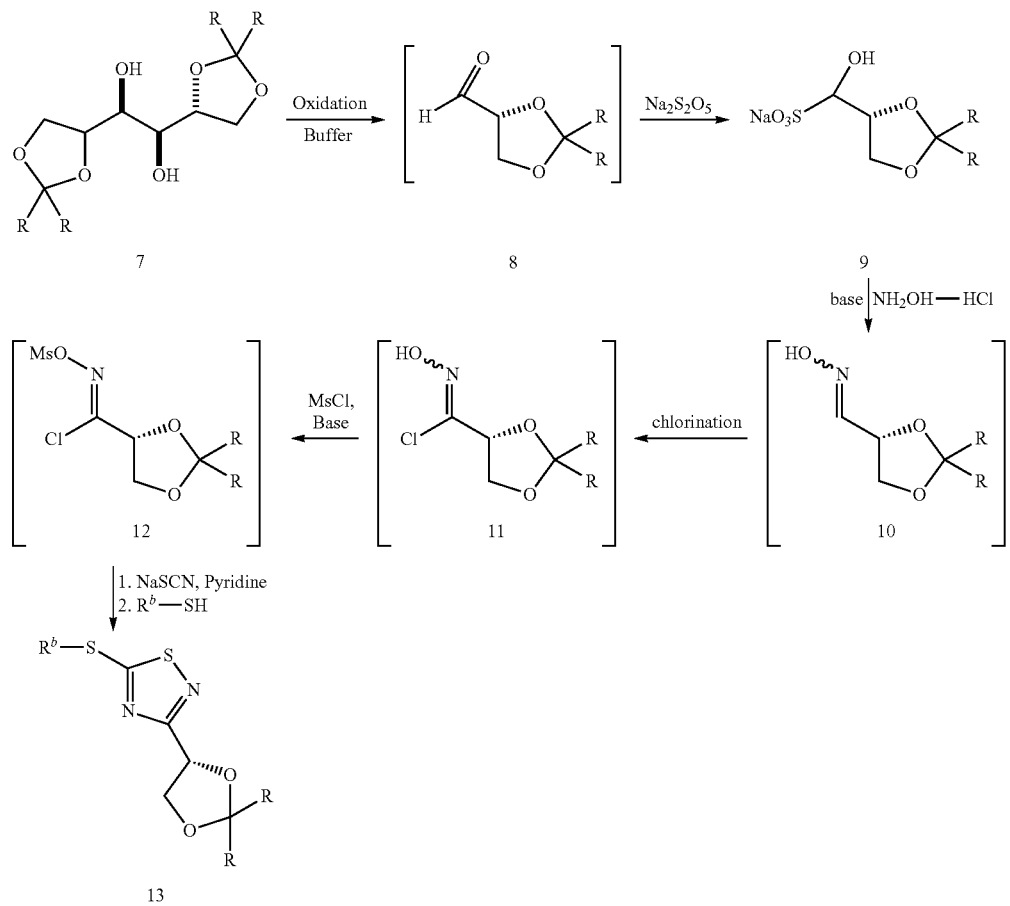

The present invention, as shown in Scheme D, involves formation of protected glyceraldehydes 9 as well as formation of the thiadiazole sulfides 13. The invention also relates to compounds where R is $C_{1-3}$ alkyl, or the two R groups together form cyclohexyl and where $R^b$ is aryl, alkyl, arylalkyl, or 5-6 membered heterocyclyl. In another embodiment of the invention, $R^b$ is $C_{6-10}$ membered aryl, $C_{1-6}$ alkyl, $C_{6-10}$ aryl-$C_{1-3}$ alkyl, 5-6 membered heteroaryl or 5-6 membered saturated or partially saturated heterocyclyl. In another embodiment of the invention, the aryl, alkyl, arylalkyl, or 5-6 membered heterocyclyl substitutents are optionally substituted with one or more substituents selected from lower alkyl, halo, haloalkyl, and the like.

Embodiments of the process include oxidative cleavage of a substituted diol 7 to give aldehyde 8. Embodiments of the process include oxidizing cleavage agent such as NaIO₄, chromic acid, or Pb(OAc)₄. In certain embodiments of the invention, NaIO₄ is used for the oxidative cleavage. Embodiments of the process include NaIO₄ in an amount of at least about 1 equivalents per mole of the diol employed. The invention also relates to the use of about 1.4-1.5 equivalents of NaIO₄.

Embodiments of the process include the oxidizing cleavage in an organic solvent, e.g. CH₂Cl₂ or EtOAc.

Embodiments of the process include an aqueous buffer such as NaHCO$_3$, at about 0.3 eq., in the presence of H$_2$O. Preferably the pH of the oxidative cleavage is maintained higher than 0.8, preferably above 3.

Treatment of an alcoholic aldehyde solution with a salt of SO$_3^{-2}$, such as Na$_2$S$_2$O$_5$, NaHSO$_3$, or Na$_2$SO$_3$, at a temperature above RT, preferably at above 35° C., more preferably at a temperature of about 50° C., provides a diastereomeric mixture of the bisulfite adduct 9. Embodiments of the process include treatment with Na$_2$S$_2$O$_5$ in an amount of about 0.5-2 equivalents per mole of the aldehyde employed. The invention also relates to the use of about 0.5 equivalents of Na$_2$S$_2$O$_5$.

Treatment of the bisulfite adduct 9 in an organic solvent, such as MeTHF, with an aqueous solution of NH$_2$OH or NH$_2$OH—HCl and a base such as K$_2$CO$_3$ or Na$_2$CO$_3$, gives the oxime 10. To the anh. oxime 10 in a solvent such as a mixture of DMAC/MeTHF, is added a catalytic amount of HCl in a solvent such as dioxane followed by halogenation, such as with Cl$_2$ or NCS, to give the corresponding chloro-oxime 11 intermediate. The chloro-oxime 11 is reacted with MsCl in the presence of base, such as DIPEA, to give the chloro-mesylate 12, at a temperature below RT, preferably at a temperature of about 0° C. Reaction of chloro-mesylate 12 with NaSCN, in a solvent such as MeTHF, at a temperature of about RT, and in the presence of organic base, such as pyridine, gives the acyl thioisocyanate intermediate. Treatment of the acyl thioisocyanate with a substituted thiol, such as toluene sulfide, in the presence of 1-2 equivalents of organic base, such as pyridine, in a non-polar solvent such as MeTHF, at a temperature below RT, preferably at about 0° C., gives 1,2,4-thiadiazole 13.

The invention also relates to a process in an atmosphere where minimal oxygen is present, such as in a N$_2$ environment.

The present invention also relates to a process where the bisulfite adduct 9 is isolated prior to the cyclization step. Alternatively, the bisulfite adduct 9 is not isolated prior to formation of the thiadiazole.

Embodiments of the process include reaction in a non-aqueous solvent environment. Such solvents include MeTHF, MTBE, IPAC, heptane, hexane, toluene, benzene, xylenes, IPA, dioxane, CH$_2$Cl$_2$, EtOH, MeCN and THF. The present invention also relates to a process where a mixture of solvents is utilized. In certain embodiments of the invention, MeTHF is used as the solvent. Where the term "non-aqueous" is used, it is not to intend that water is not generated by a reaction step.

Scheme E

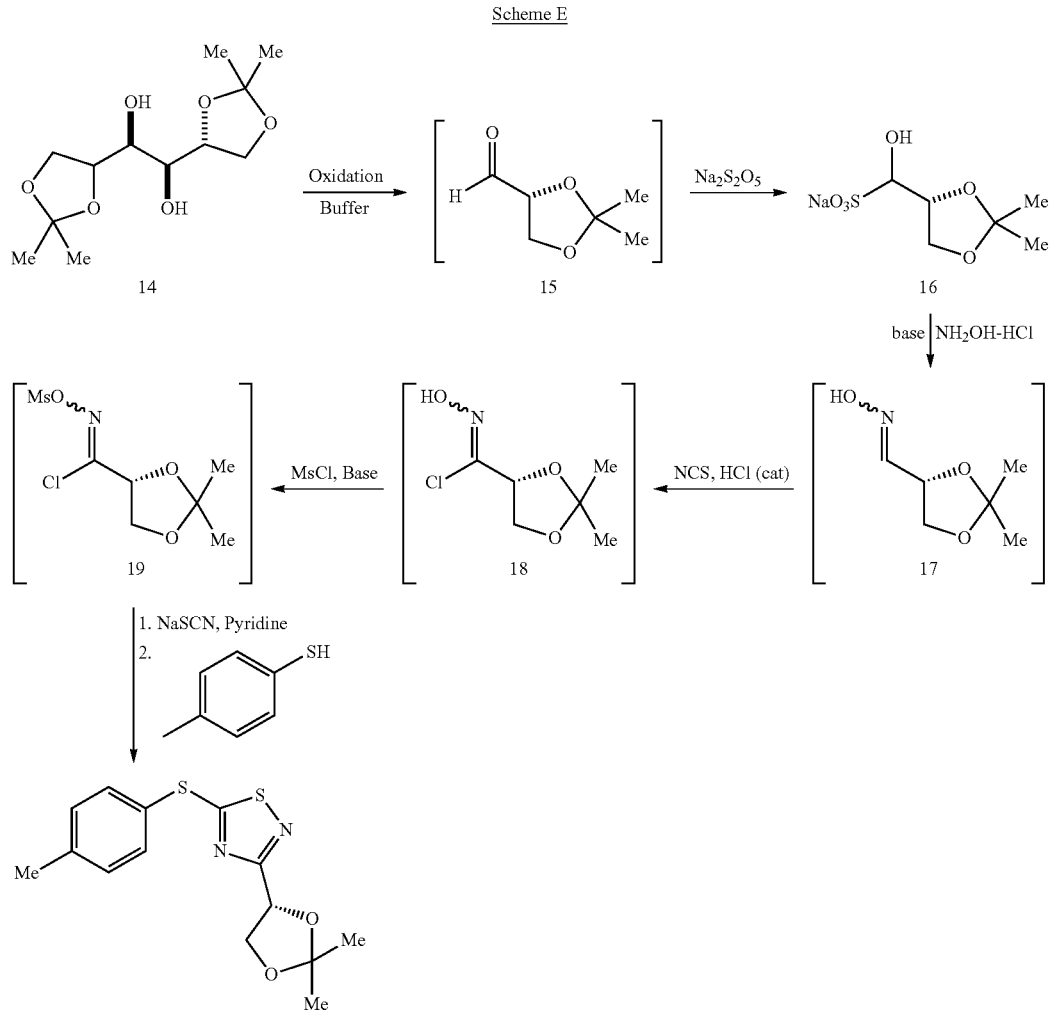

The present invention, as shown in Scheme E, involves formation of protected glyceraldehydes 16 as well as formation of the thiadiazole sulfides 20. Bisulfite adduct 16 is stable at RT up to 3 days in 10:1 EtOH/H$_2$O.

Embodiments of the process includes oxidative cleavage of 1,2,5,6-di-O-isopropylidene-D-mannitol 7 to give aldehyde 15. Embodiments of the process include oxidizing cleavage agent such as NaIO$_4$, or Pb(OAc)$_4$. In certain embodiments of the invention, NaIO$_4$ is used for the oxidative cleavage. Embodiments of the process include NaIO$_4$ in an amount of at least about 1 equivalents per mole of the diol employed. The invention also relates to the use of about 1.4-1.5 equivalents of NaIO$_4$.

Embodiments of the process include the oxidizing cleavage in an organic solvent such as CH$_2$Cl$_2$ or EtOAc.

Embodiments of the process include an aqueous buffer such as NaHCO$_3$, at about 0.3 eq., in the presence of H$_2$O. Preferably the pH of the oxidative cleavage is maintained higher than 0.8, preferably above 3.

Treatment of an alcoholic aldehyde solution with a salt of SO$_3^{-2}$, such as Na$_2$S$_2$O$_5$, NaHSO$_3$, or Na$_2$SO$_1$, at a temperature above RT, preferably at above 35° C., more preferably at a temperature of about 50° C., provides a diastereomeric mixture of the bisulfite adduct 16. Embodiments of the process include treatment with Na$_2$S$_2$O$_5$ in an amount of about 0.5-2 equivalents per mole of the aldehyde employed. The invention also relates to the use of about 0.5 equivalents of Na$_2$S$_2$O$_5$.

Treatment of the bisulfite adduct 16 in an organic solvent, such as MeTHF, an aqueous solution of NH$_2$OH—HCl and with a base such as K$_2$CO$_3$ or Na$_2$CO$_3$, gives the oxime 17. To the anh. oxime 17 in a solvent such as a mixture of DMAC/MeTHF, is added a catalytic amount of HCl in a solvent such as dioxane followed by halogenation, such as with Cl$_2$ or NCS, to give the corresponding chloro-oxime 18 intermediate. The chloro-oxime 18 is reacted with MsCl in the presence of base, such as DIPEA, to give the chloro-mesylate 19, at a temperature below RT, preferably at a temperature of about 0° C. Reaction of chloro-mesylate 19 with NaSCN, in a solvent such as MeTHF, at a temperature of about RT, and in the presence of organic base, such as pyridine, gives the acyl thioisocyanate intermediate. Treatment of the acyl thioisocyanate with a toluene sulfide, in the presence of 1-2 equivalents of organic base, such as pyridine, in a non-polar solvent such as MeTHF, at a temperature below RT, preferably at about 0° C., gives 1,2,4-thiadiazole 20.

The invention also relates to a process in an atmosphere where minimal oxygen is present, such as in a N$_2$ environment.

The present invention also relates to a process where the bisulfite adduct 16 is isolated prior to the cyclization step. Alternatively, the bisulfite adduct 16 is not isolated prior to formation of the thiadiazole.

Embodiments of the process include reaction in a non-aqueous solvent environment. Such solvents include MeTHF, MTBE, IPAC, heptane, hexane, toluene, benzene, xylenes, IPA, dioxane, CH$_2$Cl$_2$, EtOH, MeCN and THF.

The present invention also relates to a process where a mixture of solvents is utilized. In certain embodiments of the invention, MeTHF is used as the solvent. Where the term "non-aqueous" is used, it is not to intend that water is not generated by a reaction step.

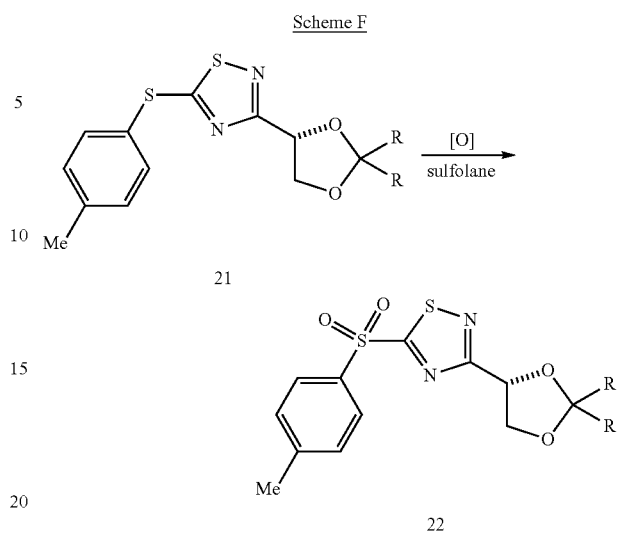

Scheme F

Oxidation of 3-[(4S)-2,2-dimethyl-1,3-dioxolan-4-yl]-5-[(4-methylphenyl)sulfanyl]-1,2,4-thiadiazole 21 is described in Scheme F. 3-[(4S)-2,2-Dimethyl-1,3-dioxolan-4-yl]-5-[(4-methylphenyl)sulfanyl]-1,2,4-thiadiazole is treated with an oxidizing agent, to provide the corresponding sulfones 22.

Embodiments of the process include an oxidizing agent selected from peroxide related agents such as urea-H$_2$O$_2$, aq H$_2$O$_2$, and peracid based reagents such as mCPBA; peracetic acid or MMPP. The invention also relates to the use of aq H$_2$O$_2$ or urea-H$_2$O$_2$.

Embodiments of the process include a peroxide related oxidizing agent in the presence of a catalyst, for example (NH$_4$)$_6$Mo$_7$O$_{24}$—(H$_2$O)$_4$. Embodiments of the process include a peroxide related oxidizing agent in the presence of a catalyst, where less than about 10 wt % of catalyst is used. Embodiments of the process include a peroxide related oxidizing agent in the presence of a catalyst, where less than about 5 wt % of catalyst is used.

Embodiments of the process include oxidation in the presence of MeCN or sulfolane.

Embodiments of the process include an oxidation carried out at a temperature of above about −15° C. and the temperature of reflux of the solution. Embodiments of the process include an oxidation carried out at a temperature of above about −15° C. and about 30° C. The invention also relates to an oxidation carried out at a temperature of above about RT.

Embodiments of the process include oxidizing agent in an amount of more than about 1 equivalents per mole of the sulfide employed. The invention also relates to the use of about 2.5 equivalents of oxidizing agent.

Scheme G

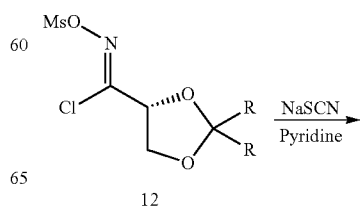

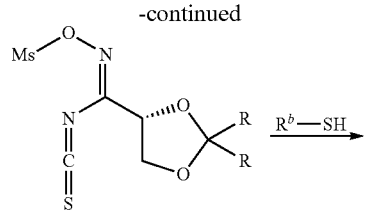

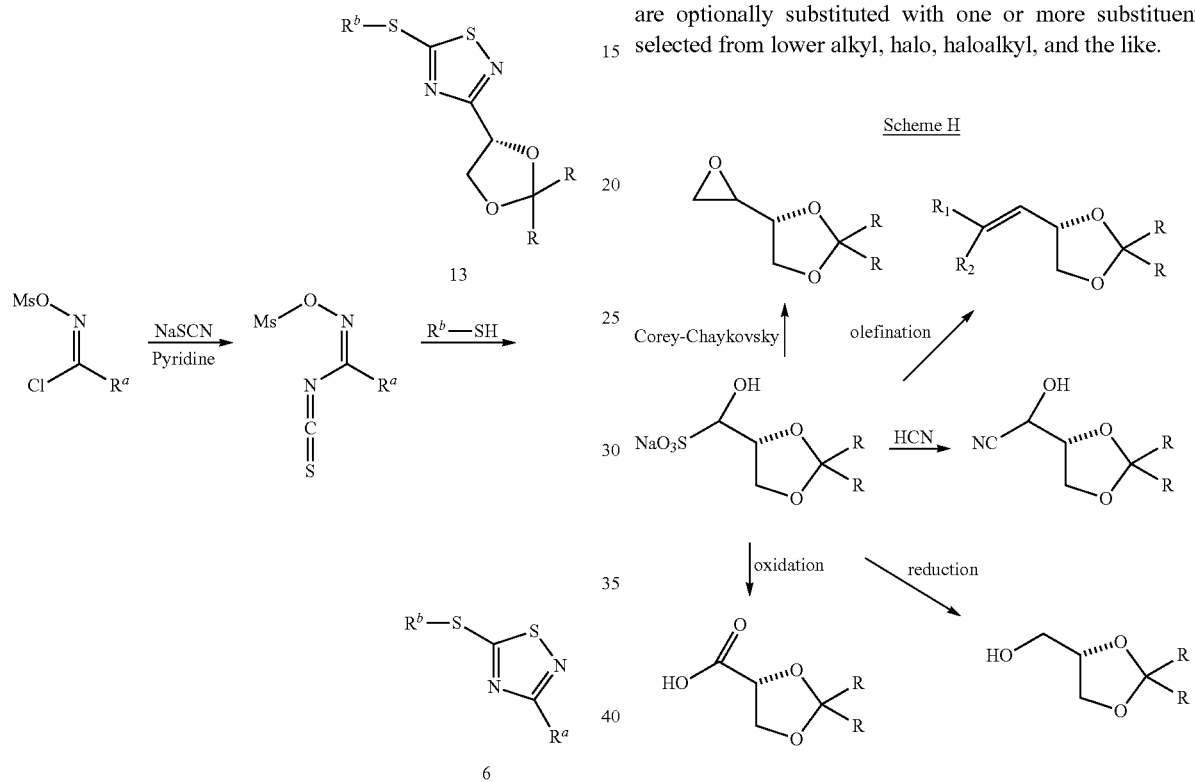

For clarification, the acyl thioisocyanate intermediate in Schemes C and D is included in Scheme G. All other reagents are described above. The present invention includes the formation of thiadiazoles from the corresponding acyl thioisocyanate upon treatment with substituted thiols, where $R^b$ is aryl, alkyl, arylalkyl, or 5-6 membered heterocyclyl. In another embodiment of the invention, $R^b$ is $C_{6-10}$ membered aryl, $C_{1-6}$ alkyl, $C_{6-10}$ aryl-$C_{1-3}$ alkyl, 5-6 membered heteroaryl or 5-6 membered saturated or partially saturated heterocyclyl. In another embodiment of the invention, the aryl, alkyl, arylalkyl, or 5-6 membered heterocyclyl substitutents are optionally substituted with one or more substituents selected from lower alkyl, halo, haloalkyl, and the like.

Such glyceraldehyde bisulfite adducts are useful in further reactions as described in Scheme H.

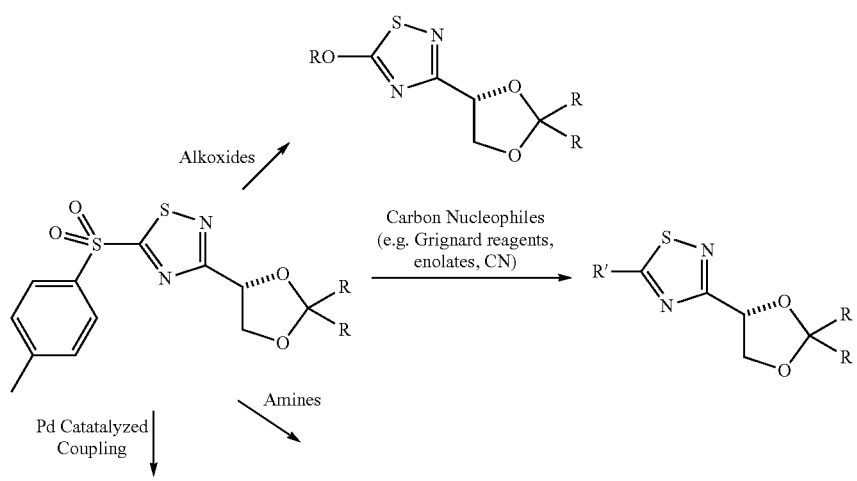

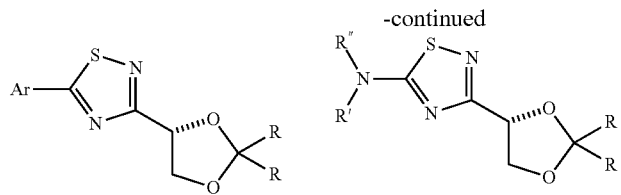

Such substituted sulfide-thiadiazoles and thiadiazole sulfones are useful in further reactions as described in Scheme I.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

The terms "aralkyl" or "arylalkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals.

More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "alkylamino" embraces "N-alkylamino" and "N,N-dialkylamino" where amino groups are substituted with one alkyl radical and with two independent alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The present invention is further defined in the following Examples, in which all parts and percentages are by weight and area percent (A %) and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLE 1 sodium [(4R)-2,2-dimethyl-1,3-dioxolan-4-yl](hydroxy)methanesulfonate

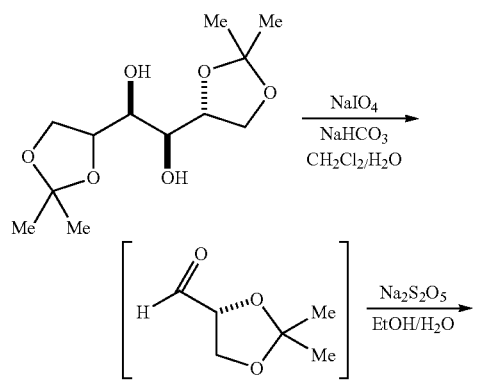

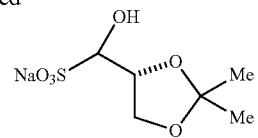

| Material | Source | Mass | Equiv |
|---|---|---|---|
| 1,2:5,6-di-O-isopropylidene-D-mannitol | TCI-Japan/Carbosynth/(1 kg)/(0.8 kg) | 1.8 kg | 1.0 |
| NaIO$_4$ | Aldrich | 2.06 kg | 1.4 |
| NaHCO$_3$, (sat. Aq. solution) | TekNova | 0.72 L | 0.12 |
| CH$_2$Cl$_2$ | Aldrich | 18 L | |
| MgSO$_4$(anh.) | Aldrich | 0.9 kg | 1.0 |
| EtOH | Aldrich, denatured, 90% EtOH, 5% MeOH, 5% iPrOH | 10 L | |
| Na$_2$S$_2$O$_5$ | Alfa Aesar | 0.940 kg | 0.5 |
| Deionized H$_2$O | | 2 L | |
| EtOH | Aldrich, denatured, 90% EtOH, 5% MeOH, 5% iPrOH | 20 L | |

Note:
Volumes indicated are relative to 1,2:5,6-di-O-isopropylidene-D-mannitol unless otherwise noted.

Step 1—Diol Cleavage

Blanket reactor with N$_2$. A N$_2$ atmosphere is kept on reactor during entire process. Set jacket to 20±5° C. Charge 1,2:5,6-di-O-isopropylidene-D-mannitol (1.8 kg) to reactor. Charge CH$_2$Cl$_2$ (18 L, 10±0.5 vol relative to 1,2:5,6-di-O-isopropylidene-D-mannitol) to reactor. Start agitation (450 RPM). Charge sat. aqueous NaHCO$_3$ (0.72 L, 0.4±0.05 vol relative to 1,2:5,6-di-O-isopropylidene-D-mannitol) to reactor. Charge NaIO$_4$ (2.06 kg) to reactor portion-wise, so that temperature does not exceed 35±5° C. Agitate at 20±5° C. for >60 min. Charge anh. MgSO$_4$ (0.9 Kg, 50 wt % to 1,2:5,6-di-O-isopropylidene-D-mannitol) to reactor so that temperature does not exceed 30° C. Agitate at 20±5° C. for >15 min. Remove solids by filtration. Transfer 'aldehyde solution' to a clean dry container.

Step 2—Bisulfite Adduct Formation

Set jacket to 20±5° C. Charge 'aldehyde solution' to reactor. Configure reactor for distillation. Set jacket to 45±5° C. Collect 16.6 kg (12.6 L, 7±0.5 vol to 1,2:5,6-di-O-isopropylidene-D-mannitol) distillate. Charge EtOH (7.1 kg, 9.0 L, 5±0.5 vol to 1,2:5,6-di-O-isopropylidene-D-mannitol) to reactor. Collect 11.9 kg (9.0 L, 5±0.5 vol to 1,2:5,6-di-O-isopropylidene-D-mannitol) distillate. Break vacuum to reactor, back fill with N$_2$. Charge EtOH (14.6 L, to bring to a desired volume to obtain 10:1 EtOH/water ratio, 20 L) to reactor; maintain a rate such that the temperature does not go below 40±5° C. Set internal temperature to 50±2° C. Charge Na$_2$S$_2$O$_5$ (0.96 kg±0.5%) to appropriate container. Charge DI H$_2$O (2 L) to container containing Na$_2$S$_2$O$_5$. The Na$_2$S$_2$O$_5$ solution must be freshly prepared. Charge Na$_2$S$_2$O$_5$ solution to reactor via addition funnel over 30-45 min. Agitate at 50±5° C. for 2 h. Cool reaction mixture to 20±5° C. over a least 30 min. Age reaction mixture at 20±5° C.>2 h. Collect solids by filtration [Aurora filter with 12 micron Teflon filter cloth]. Rinse reactor and cake with EtOH (4.5 L, 2.5 vol to 1,2:5,6-di-O-isopropylidene-D-mannitol). Dry solids on funnel under dry N$_2$ to constant weight. For 1800 g (1,2:5,6-di-O-isopropylidene-D-mannitol) pilot: 2216 g of sodium

[(4R)-2,2-dimethyl-1,3-dioxolan-4-yl](hydroxy)methanesulfonate was obtained as a white crystalline solid. 69% overall yield.

EXAMPLE 2 sodium (2R)-1,4-dioxaspiro[4.5]dec-2-yl(hydroxy)methanesulfonate

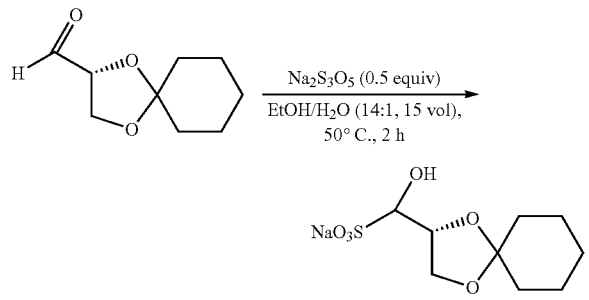

Materials:

| Material | Source | Mass (Volume) | Equiv |
|---|---|---|---|
| (2R)-1,4-dioxaspiro[4.5]dec-2-yl(hydroxy)methanesulfonate | Louston (66.7 wt %, assumed 100 wt %) | 247 g | 1.0 |
| $Na_2S_2O_5$ | Alfa Aesar | 128.5 g | 0.47 |
| EtOH (denatured) | Aldrich, | 3.5 L | |
| DI $H_2O$ | | 0.30 L | |

Procedure:

Blanket reactor with $N_2$. A $N_2$ atmosphere is kept on reactor during entire process. Set jacket to 20±5° C. Charge aldehyde (247 g, 66.7 wt %, assumed 100 wt %) to appropriate container. Charge EtOH (1.0 L) to container containing aldehyde 1, label as 'aldehyde solution. Charge 'aldehyde solution' to reactor. Rinse aldehyde container with EtOH (1.0 L) and charge rinse to reactor. Charge remaining EtOH (1.5 L) to reactor. Start agitation (250 RPM). Set internal temperature to 50±5° C. Charge $Na_2S_2O_5$ (128.5 g) to appropriate container. Charge DI $H_2O$ (0.30 L) to container containing $Na_2S_2O_5$. Charge $Na_2S_2O$. solution to reactor via addition funnel. Agitate at 50±5° C. for 2 h. Cool reaction mixture to 20±5° C. over a time period of >90 min. Age reaction mixture at 20±5° C. >2 h. Collect solids by filtration. Rinse reactor and cake with EtOH (2×0.6 L). Dry solids on funnel under dry $N_2$ to constant weight. Sodium (2R)-1,4-dioxaspiro[4.5]dec-2-yl(hydroxy)methanesulfonate (335.6 g) was obtained as a white crystalline solid. 84% yield.

EXAMPLE 3

3-[(4S)-2,2-Dimethyl-1,3-dioxolan-4-yl]-5-[(4-methylphenyl)sulfanyl]-1,2,4-thiadiazole

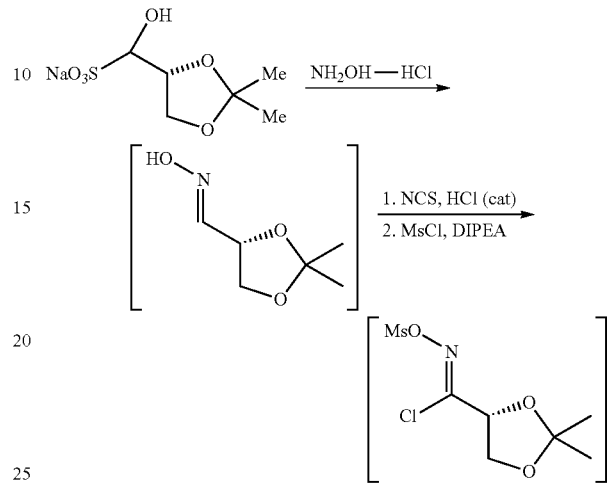

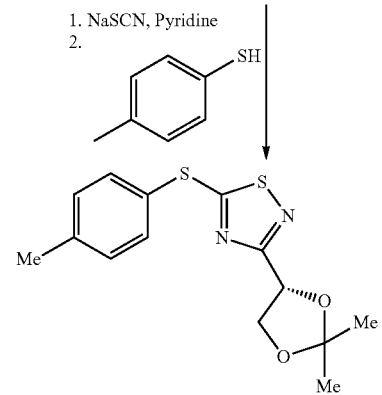

| Material | Eq | Volumes (relative to SM) | Mass | Volume |
|---|---|---|---|---|
| sodium [(4R)-2,2-dimethyl-1,3-dioxolan-4-yl](hydroxy)methanesulfonate | 1.0 | | 16.2 kg | |
| MeTHF | | 4 | 54.7 kg | 64.0 L 32.25 L |
| Water | | 1.6 | 25.6 kg | 25.6 L |
| $K_2CO_3$ | 1.2 | | 11.3 kg | |
| $NH_2OH$ HCl | 1.15 | | 5.46 kg | |
| MeTHF | | 3 | 41.0 kg | 48.0 L |
| MeTHF | | 3 | 41.0 kg | 48.0 L |
| MeTHF | | 0.5 | 6.83 kg | 8.0 L |
| MeTHF | | 0.5 (rel to oxime) | 4.3 kg | 5.0 L |
| (S)-2,2-dimethyl-1,3-dioxolane-4-carbaldehyde oxime STEP 2 | 1.0 | | 9.33 kg | |
| MeTHF | | 8.5 (total) | 67.7 kg | 52.57 L |
| DMAC | | 1 | 8.77 kg | 9.33 L |
| 4.0M HCl in 1,4-dioxanes | 0.02 | | | 323 mL |
| NCS | 1.05 | | 9.0 kg | |

-continued

| Material | Eq | Volumes (relative to SM) | Mass | Volume |
|---|---|---|---|---|
| MsCl | 1.05 | | 7.73 kg | 5.22 L |
| DIPEA | 1.1 | | 9.14 kg | 12.32 L |
| Water | | 2 | 18.6 kg | 18.6 L |
| Water | | 1 | 9.3 kg | 9.3 L |
| Sat. Brine | | 1 | 10.5 kg | 9.3 L |
| Water | | 1 | 9.3 kg | 9.3 L |
| Sat. Brine | | 1 | 10.4 kg | 9.3 L |
| MeTHF | | 4 | 31.9 kg | 37.25 L |
| MeTHF | | 4 | 31.8 kg | 32.25 L |
| MeTHF | | 0.5 (rel to Cl-Ms) | 7.5 kg | 8.8 L |
| MeTHF | | 0.5 (rel to Cl-Ms) | 4 kg | 4.68 L |
| (R)-2,2-dimethyl-N-(methylsulfonyloxy)-1,3-dioxolane-4-carbimidoyl chloride solution in MeTHF STEP 3 | 1.0 | | 15.0 kg | |
| NaSCN | 1.1 | | 5.2 kg | |
| MeTHF | | 6.5 | 83.3 kg | 97.5 L |
| Pyridine | 2.0 | | 9.2 kg | 9.4 L |
| MeTHF | | | | 4.0 L |
| Toluene thiol | 1.1 | | 7.95 kg | |
| MeTHF | | 1 | | 12 L |
| MeTHF | | ≤1 | | 3 L |
| Sat. NaHCO₃ | | 3 | | 45 L |
| Water | | 2 | 30 kg | 30 L |
| Sat. Brine | | 2 | | 30 L |
| Water | | 4 | 60 kg | 60 L |
| IPA | | 5 | 58.9 kg | 75 L |
| IPA | | | 19.8 kg | 25 L |
| Sulfide (seed) | 0.01 | | | |
| IPA | | 2 | | 60 L |
| IPA | | 2 | | 30 L |

Oxime Formation

Charge sodium [(4R)-2,2-dimethyl-1,3-dioxolan-4-yl](hydroxy)methanesulfonate (16.2 kg) to a clean, dry 250 LJR. Charge MeTHF (94.7 kg) to 250 LJR. Stir at 25±5° C. under N₂. Charge water (25.6 kg) to a 100 LJR. Charge potassium carbonate (11.3 kg) to the 100 LJR. Stir mixture in 100 LJR until homogeneous. Charge hydroxylamine hydrochloride (5.46 kg) to 100 LJR. Stir until mixture is homogeneous at 20±5° C. Charge potassium carbonate aqueous solution from 100 LJR to 250 LJR, maintaining batch temperature≤30° C. Stir batch in 250 LJR for ≥1 hour at 20±5° C. Stir batch for ≥1 hour. Stop agitation and allow >5 min. for phase separation. Phase cut and remove aqueous layer. Hold product solution in MeTHF overnight in 250 LJR at <10° C. Remove THF under vacuum at 30±5° C. batch temperature until ~1.5-2 volumes remain. Charge MeTHF (41 kg) to 250 LJR. Remove THF under vacuum at 30±5° C. batch temperature until ~1.5-2 volumes remain. Charge MeTHF (41 kg) to 250 LJR. Remove MeTHF under vacuum at 30±5° C. batch temperature until ~1.5-2 volumes remain. Filter contents of 250 LJR through a 5 micron filter into a preweighed carboy. Charge MeTHF (4.3 kg) to 250 LJR. Stir MeTHF in 250 LJR. Filter contents of 250 LJR through a 5 micron filter into a preweighed carboy. Clean 250 LJR with water, acetone and final rinse of MeTHF. Transfer contents of carboy to clean dry 250 LJR. Charge MeTHF (3.95 kg) rinse to carboy. Transfer contents of carboy to 250 LJR. Hold product solution in 250 LJR at <10° C. Yield of oxime—94.2%.

Chloromesylate [Cl-Ms] Formation

Charge MeTHF (47 kg) to 250 LJR containing oxime solution. Stir MeTHF in 250 LJR. Charge DMAC (9.3 L) to 250 LJR. Charge 4.0 M HCl in dioxanes (323 mL) to 250 LJR. Charge NCS (9.0 kg) to reaction vessel in 10 equal portions, maintaining an internal temperature 15±5° C. Stir batch for >30 min. at 20±5° C. Cool contents of 250 LJR to 0±5° C. Charge MsCl (7.73 kg) to 250 LJR. Charge DIPEA (9.15 kg) to addition funnel. Add DIPEA to 250 LJR over ≥30 min., maintaining an internal temperature≤10° C. Stir contents for >1 hour at 0±5° C. Warm Reaction Vessel contents to 20±5° C. Charge water (18.6 kg) to 250 LJR. Stir mixture ≥5 min. Stop agitation and allow >5 min. for phase separation. Reaction mixture becomes biphasic. Remove lower, aqueous layer. Charge water (8.3 kg) to 250 LJR. Charge sat. brine (10.5 kg) to 250 LJR. Stir 250 LJR≥5 min. at 20±5° C. Stop agitation and allow >5 min. for phase separation. Remove lower, aqueous layer. Charge water (9.3 kg) to 250 LJR. Charge sat. brine (10.4 kg) to 250 LJR. Stir 250 LJR≥5 min. at 20±5° C. Stop agitation and allow >5 min. for phase separation. Remove aqueous layer. Remove MeTHF under vacuum at 30±5° C. batch temperature until ~1.5-2 volumes remain. Charge MeTHF (31.9 kg) to 250 LJR. Remove MeTHF under vacuum at 30±5° C. batch temperature until ~1.5-2 volumes remain. Charge MeTHF (31.8 kg) to 250 LJR. Remove MeTHF under vacuum at 30±5° C. batch temperature until ~1.5-2 volumes remain. Filter contents of 60 LJR through a 5 micron filter into a preweighed carboy. Charge MeTHF (7.5 kg) to 250 LJR. Stir MeTHF in 250 LJR. Filter through a 5 micron filter.

Step 5: Sulfide Formation

Charge NaSCN (5.208 kg) to a clean, dry 250 LJR. Charge MeTHF (83.35 kg) to 250 LJR. Charge pyridine (9.4 L) to 250 LJR. Initiate agitation in 250 LJR. Adjust 250 LJR internal temperature to 20±5° C. Transfer the chloromesylate solution to 100 LJR maintaining batch temperature of 20±5° C. Color changes to orange. Stir contents of 250 LJR for >2 hours at 20±5° C. Cool contents of 250 LJR to 0±5° C. Charge toluene thiol (7.95 kg) to a clean container. Charge MeTHF (12 L) to "Toluene Thiol Solution". Agitate mixture until homogeneous. Charge "Toluene Thiol Solution" to 250 LJR, keeping batch temperature≤10° C. Stir contents of 250 LJR for >2 h. at 0±5° C. Warm reaction vessel contents to 20±5° C. Charge sat. aqueous NaHCO₃ (45 L) to 250 LJR. Stir mixture at 20±5° C.≥5 min. Stop agitation and allow >5 min. for phase separation. Remove lower, aqueous layer. Charge water (30 kg) to 250 LJR. Charge sat. brine (30 L) to 250 LJR. Stir mixture ≥5 min. Stop agitation and allow >5 min. for phase separation. Remove lower, aqueous layer. Charge water (60 kg) to 250 LJR. Stir mixture at 20±5° C. for ≥5 min. Stop agitation and allow >5 min. for phase separation. Remove lower, aqueous layer. Remove MeTHF under vacuum at 30±5° C. batch temperature until ~1.5-2 volumes remain. Charge IPA (58.9 kg) to 250 LJR. Remove IPA under vacuum at 30±5° C. batch temperature until ~1.5-2 volumes remain. Charge IPA (19.8 kg) to 250 LJR to reach a total batch volume of 64 L. Heat batch to 50±5° C. Cool batch to 40±2° C. Charge seed (1%) as a slurry in IPA (4 vol wrt seed). Stir batch at 40±2° C. for >15 min. Cool reaction vessel contents to 0±5° C. over ≥4 h. Hold reaction vessel contents at 0±5° C. for ≥2 h. Filter contents of 250 LJR on a 20" Aurora filter using Teflon 12-25 micron filter cloth sending the liquor to an appropriate vessel. Collect and weigh filtrate. Cool the IPA in vessel to 0±5° C. Charge cold IPA to 250 LJR. Stir the rinse for >5 min. at 0±5° C. Send the wash onto the filter cake and through to an appropriate vessel. Collect and weigh filtrate. Charge IPA (30 L) to 250 LJR. Cool the IPA in 250 LJR to 0±5° C. Stir the rinse for >5 min. at 0±5° C. Send the wash onto the filter cake and through to an appropriate vessel. Dry filter cake for ≥24 h. under $N_2$ at 20±5° C. Sulfide (15.4 Kg) was isolated in 72.1% overall yield.

EXAMPLE 4

3-[(4S)-2,2-Dimethyl-1,3-dioxolan-4-yl]-5-[(4-methylphenyl)sulfonyl]-1,2,4-thiadiazole

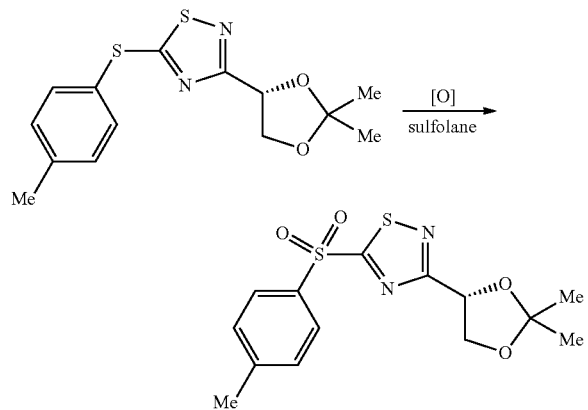

Catalyst

| Step | Material | Eq | Volumes (relative to SM) | Mass | Volume |
|---|---|---|---|---|---|
| 1 | Ammonium molybdate tetrahydrate | 1 | — | 802 g | — |
| 2 | Water | — | 4 | 3.2 kg | 3.2 L |
| 3 | Urea hydrogen peroxide adduct | 14 | — | 856 g | — |
| 4 | 3-[(4S)-2,2-dimethyl-1,3-dioxolan-4-yl]-5-[(4-methylphenyl)sulfanyl]-1,2,4-thiadiazole | 1 | — | 15.0 kg | — |
| 5 | Sulfolane | — | 5 | 92.3 kg | 75 L |
| 6 | Catalyst sol'n from steps 1-4 | — | — | 3.65 kg | — |
| 7 | Urea hydrogen peroxide adduct | 0.313 | — | 1.43 kg | — |
| 8 | Urea hydrogen peroxide adduct | 0.313 | — | 1.43 kg | — |
| 9 | Urea hydrogen peroxide adduct | 0.625 | — | 2.86 kg | — |
| 10 | Urea hydrogen peroxide adduct | 0.625 | — | 2.86 kg | — |
| 11 | Urea hydrogen peroxide adduct | 0.625 | — | 2.86 kg | — |
| 12 | 1.0M pH 4 NaOAc buffer solution | | | | 15.0 L |
| 13 | 3-[(4S)-2,2-dimethyl-1,3-dioxolan-4-yl]-5-[(4-methylphenyl)sulfonyl]-1,2,4-thiadiazole | 0.01 | | 75 g | |
| 14 | 1.0M pH 4 NaOAc buffer solution | | | | 97.5 L |
| 15 | 1.0M aqueous sodium thiosulfate | 0.19 | | | 9.72 L |
| 16 | water | | | 75 kg | 75 L |
| 17 | water | | | 75 kg | 75 L |

Preparation

Charge ammonium molybdate-tetrahydrate (802 g, 0.013 equiv) to a 5 L RBF equipped with a temperature probe and stirring. Charge water (3.2 kg) to 5 L RBF. Initiate agitation. Charge urea-$H_2O_2$ (856 g, 0.19 equiv) portion wise to 5 L RBF maintaining batch temperature 30±5° C.

Reaction

Set jacket of a clean, dry 250 LJR to 25° C. Charge 3-[(4S)-2,2-dimethyl-1,3-dioxolan-4-yl]-5-[(4-methylphenyl)sulfanyl]-1,2,4-thiadiazole (15.0 kg, 1.0 equiv) to the 250 LJR as a solid. Charge sulfolane (92.3 kg) to 250 LJR. Ensure agitator will turn freely and then initiate agitation in 250 LJR. Initiate $N_2$ Sweep. Adjust the batch temperature to 30±5° C. Charge the aqueous catalyst solution (3.65 kg) from 5 L RBF to 250 LJR. Charge first portion of urea-$H_2O_2$ (1.43 kg, 12.5% of total) to the 250 LJR as a solid. Agitate batch at 30±5° C. for >30 min. Charge urea-$H_2O_2$ (1.43 kg, 12.5% of total) to 250 LJR as a solid. Agitate batch at 30±5° C. for >30 min. Charge urea-$H_2O_2$ (2.86 kg, 25% of total) to 250 LJR as a solid. Agitate batch at 30±5° C. for >30 min. Charge urea-$H_2O_2$ (2.86 kg, 25% of total) to 250 LJR as a solid. Agitate batch at 30±5° C. for >30 min. Charge urea-$H_2O_2$ (2.86 kg, 5% of total) to 250 LJR as a solid. Agitate batch at 30±5° C. for >6 h.

Isolation

Set the jacket of the 250 L reactor to 25° C. Charge 1.0 M pH 4 NaOAc buffer solution (15 L) to 250 LJR. Charge seed (1 mol % of sulfone) in a 1:1 sulfolane buffer mixture (4 vol wrt seed). Agitate batch at 25±5° C. for >30 min. Charge 1.0 M pH 4 NaOAc buffer solution (97.5 L) to 250 LJR over >1 h. Charge sodium thiosulfate solution (9.72 L) to 250 LJR maintaining batch temperature<30° C. Agitate batch at 25±5° C. for >15 min. Filter contents of 250 LJR on a 20" Aurora filter equipped with a 12-20 μm PTFE cloth. Charge water (75 kg) rinse to 250 LJR. Stir contents of 250 LJR for >1 min. Transfer contents of 250 LJR to filter cake and agitate for >15 mins before collecting filtrate. Wash filter cake with water (75 kg) and agitate for >15 mins before collecting filtrate. Dry filter cake under $N_2$ at ambient temperature. Transfer filter cake to the double cone dryer. Dry the filter cake at elevated temperature and reduced pressure. Note: on 15 kg scale, 15.4 kg of sulfone isolated (91.9%)

Alternatively, oxidation was tried via treatment of the sulfide with the following reagents and solvents and the corresponding results:

| Reagent | Result |
|---|---|
| mCPBA, DCM | Clean oxidation, high assay yld, no deprotection |
| MMPP, MeOH | Clean oxidation, high assay yld, no deprotection |
| Peracetic acid | Oxidation, predominantly deprotection |
| Oxone, aqueous acetone | decomposition |
| Ozone, MeOH | No significant reaction |
| Sodium perborate, MeCN/water | No significant reaction |
| NMO, TPAP, MeCN | 10% Oxidation |
| NMO, $NaWO_4$, MeOH | No significant reaction |
| aq $H_2O_2$, $NaWO_4$, MeOH | 20-30% Oxidation, slow deptotection |
| aq $H_2O_2$, $MoO_2Cl_2$, MeCN | No significant oxidation, rapid deprotection |
| $MoO_2(acac)_2$, DCM, TBHP/decane | Slow oxidation, slow deprotection |
| aq $H_2O_2$, Ammonium molybdate, MeOH | 75-80% Oxidation, slow deprotection |

The following examples describe other thiadiazoles formed via the current method detailed above.

EXAMPLE 5

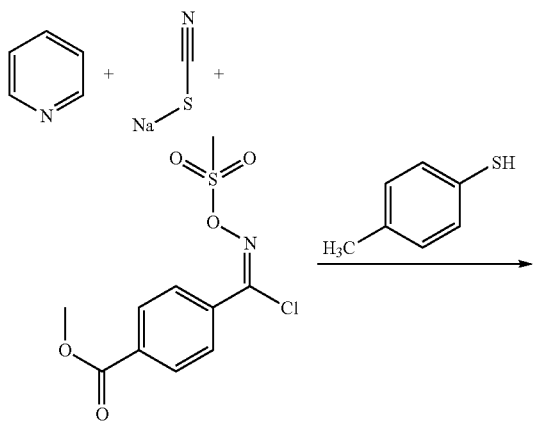

(E)-Methyl 4-(chloro(((methylsulfonyl)oxy)imino)methyl)benzoate (Prep. 1) (510 mg), NaSCN (208 mg), MeCN (5 mL) and pyridine (0.56 mL) were stirred at 40 C for about 6 h. Toluene thiol (320 mg) was added as a solid and the reaction was stirred for about 13 h. The mixture was worked up into EtOAc and methyl 4-(5-(p-tolylthio)-1,2,4-thiadiazol-3-yl)benzoate was crystallized 390 mg (66%) from EtOAc/hexanes from first crop. An additional 100 mg (17%) were purified by column chromatography (DCM-5% EtOAc/DCM). Total yield 490 mg (83%).

EXAMPLE 6

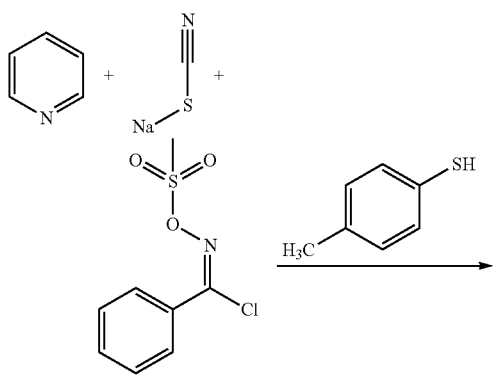

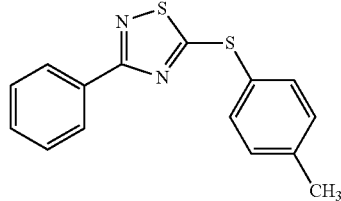

(E)-N-((Methylsulfonyl)oxy)benzimidoyl chloride (0.5 g), NaSCN (265 mg), MeCN (5 mL) and pyridine (0.7 mL) were heated to 40 C. After about 7 h., TolSH (399 mg) was added and the reaction was stirred at RT, overnight. The mixture was worked up into DCM, dried over MgSO$_4$ and the solvent was removed. The mixture was purified via column chromatography (heptane→50% DCM/heptane). 3-Phenyl-5-(p-tolylthio)-1,2,4-thiadiazole was isolated as a colorless solid (486 mg, 80%).

EXAMPLE 7

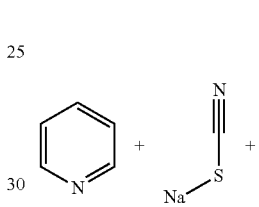

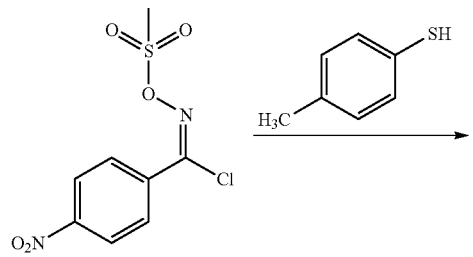

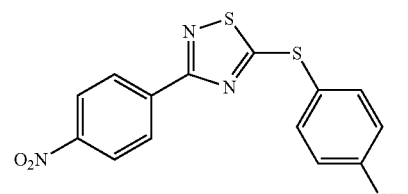

(E)-N-((Methylsulfonyl)oxy)-4-nitrobenzimidoyl chloride (0.5 g), NaSCN (215 mg), MeCN (5 mL) and pyridine (0.7 mL) were combined and heated to 40 C. After about 5 h., the reaction was quenched with toluene thiol (330 mg). The mixture was worked up into DCM, dried over MgSO$_4$ and solvent was removed. 3-(4-Nitrophenyl)-5-(p-tolylthio)-1,2,4-thiadiazole was isolated as crystalline material from DCM/heptane (370 mg, 63%). The remaining solution was purified by chromatography (heptane→DCM) to give 116 mg. Total recovered 486 mg (82%).

EXAMPLE 8

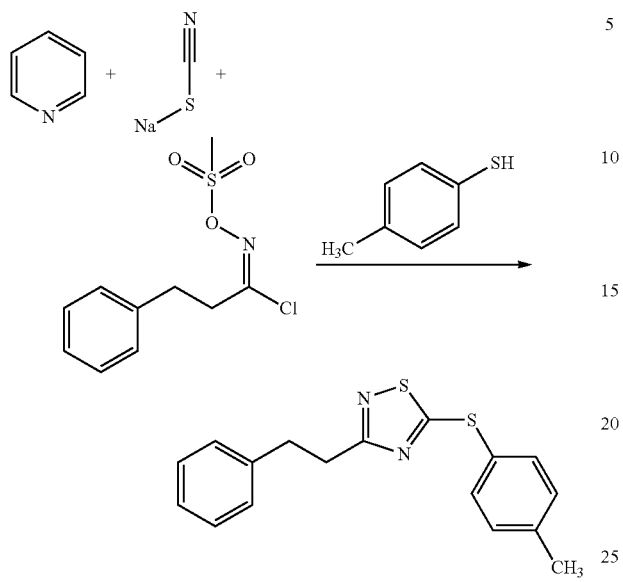

(E)-N-((Methylsulfonyl)oxy)-3-phenylpropanimidoyl chloride (511 mg), NaSCN (240 mg), MeCN (5 mL) and pyridine (660 mg) were combined and the reaction was stirred at 40 C. After about 2 h., the mixture was cooled to 0 C and toluene thiol (340 mg) was charged as a solid. The mixture became very thick, and MeCN (2.5 mL) was added. The resulting 3-phenethyl-5-(p-tolylthio)-1,2,4-thiadiazole was purified by chromatography (Hexane→50% DCM/hexane) to yield 388 mg (64%).

EXAMPLE 9

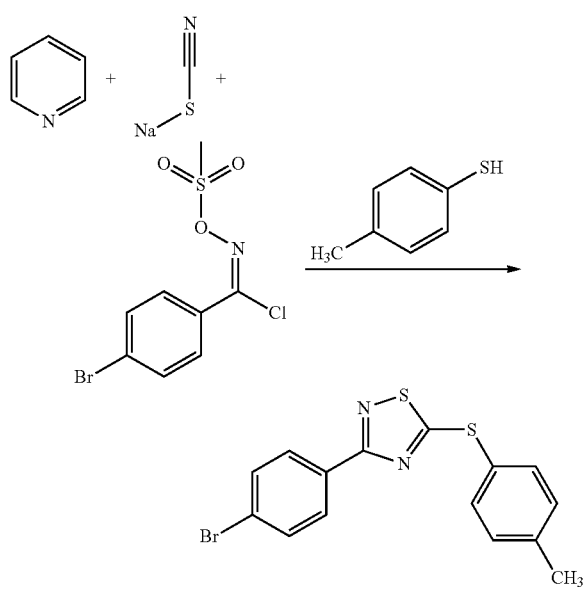

(E)-4-Bromo-N-((methylsulfonyl)oxy)benzimidoyl chloride (0.51 g), NaSCN (200 mg), MeCN (5 mL) and pyridine (0.52 mL) were combined and warmed to 40 C. After 6 h., the mixture was cooled to 0 C and toluene thiol (amount) was added TolSH as a solid. The mixture was worked up into DCM, washed with water (3×), brine (1×), dried (MgSO$_4$) and evaporated to induce crystallization. The resulting crystalline material was filtered and washed with hexane/DCM. The remaining liquid was evaporated to a yellow oil and purified by chromatography (hexane→50% DCM/hexane) to provide 3-(4-bromophenyl)-5-(p-tolylthio)-1,2,4-thiadiazole 390 mg (66%).

Preparation 1

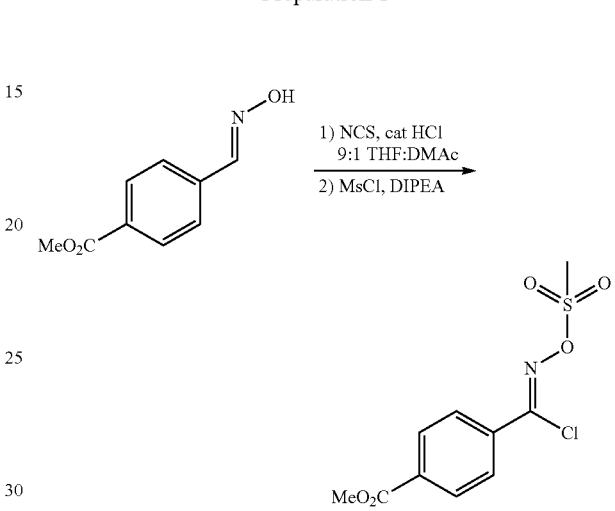

Preparation of methyl 4-[(Z)-chloro{[(methylsulfonyl)oxy]imino}methyl]benzoate

To a solution of methyl 4-[(E)-(hydroxyimino)methyl]benzoate (6.3 g, 39 mmol) in 2-methyltetrahydrofuran (60 mL) and of dimethyl acetamide (7 mL) was added a solution of HCl in dioxane (4.0 M, 195 uL, 0.78 mmol) and the mixture was cooled in an ice bath. NCS (5.48 g, 41.0 mmol) was added portionwise maintaining the internal temperature below 10 C. The mixture was stirred at 20 C for 30 min and then was cooled in an ice bath. MsCl (4.7 g, 41 mmol) was added followed by DIPEA (5.55 g, 43 mmol) dropwise maintaining the internal temperature below 10 C. The mixture was warmed to 20 C and stirred for 1 h. The reaction was partitioned between EtOAc and water and the organic layer was washed with water (3×), brine (1×), dried over MgSO$_4$ and the solvent removed to give a colorless solid (5.52 g, 54% yld).

The following were prepared using a procedure similar to that described for Preparation 1:

(E)-N-((Methylsulfonyl)oxy)benzimidoyl chloride;
(E)-N-((Methylsulfonyl)oxy)-4-nitrobenzimidoyl chloride;
(E)-N-((Methylsulfonyl)oxy)-3-phenylpropanimidoyl chloride; and
(E)-4-Bromo-N-((methylsulfonyl)oxy)benzimidoyl chloride.

As used herein and in the appended claims, the singular forms "a," "an," and "the" include the plural reference unless the context clearly indicates otherwise. Thus, for example, a reference to "a compound" is a reference to one or more compounds and equivalents thereof known to those skilled in the art, and so forth. The term "comprising" is meant to be open ended, including the indicated component but not excluding other elements.

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in their entireties.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of the structure

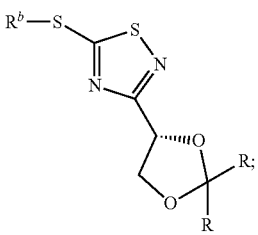

Wherein R is alkyl, aryl or the two R groups together form cycloalkyl; and
$R^b$ is an optionally substituted substituent selected from aryl, alkyl, arylalkyl, and 5-6 membered heterocyclyl.

2. A compound of claim 1 wherein R is $C_{1-6}$ alkyl or together forms $C_{3-6}$ cycloalkyl; and $R^b$ is optionally substituted phenyl.

3. A process for the preparation of

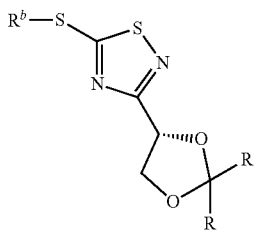

wherein R is optionally substituted aryl or alkyl, or the two R groups together form cycloalkyl or spirocycloalkyl; and
$R^b$ is optionally substituted aryl, alkyl, optionally substituted arylalkyl or optionally substituted 5-6 membered heterocyclyl;
comprising
treating

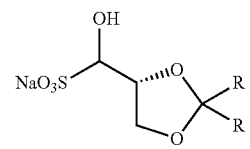

with $NH_2OH$ to form

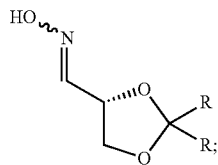

chlorination of

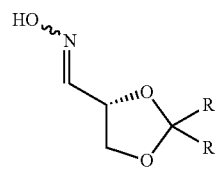

followed by treatment with MsCl to form

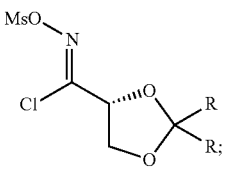

treatment of

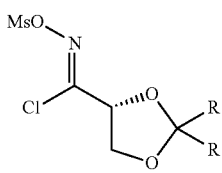

with thiocyanate to form

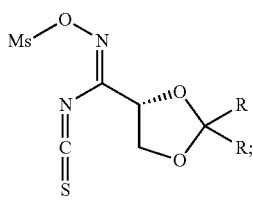

and
treatment of

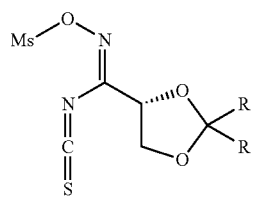

with $R^b$—SH.

4. The process of claim 3, wherein R is $C_{1-3}$ alkyl, or the two R groups together form cyclohexyl; and $R^b$ is optionally substituted aryl.
5. The process of claim 4, wherein each R is methyl and $R^b$ is 4-methylphenyl, wherein said process is for the formation of
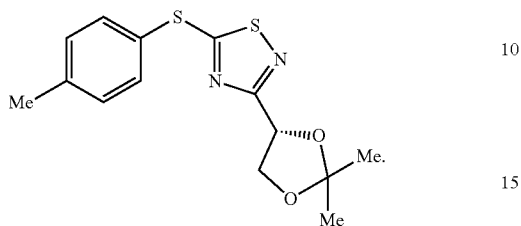
* * * * *